United States Patent
Shahriari

(10) Patent No.: US 10,478,320 B2
(45) Date of Patent: Nov. 19, 2019

(54) MODULAR ENDO-AORTIC DEVICE FOR ENDOVASCULAR AORTIC REPAIR OF DISSECTIONS AND BEING CONFIGURED FOR ADAPTABILITY OF ORGANS OF VARIOUS ANATOMICAL CHARACTERISTICS AND METHOD OF USING THE SAME

(71) Applicant: Aortic Innovations, LLC, Boca Raton, FL (US)

(72) Inventor: Ali Shahriari, Boca Raton, FL (US)

(73) Assignee: Aortic Innovations, LLC, Boca Raton, FL (US)

(*) Notice: Subject to any disclaimer, the term of this patent is extended or adjusted under 35 U.S.C. 154(b) by 229 days.

(21) Appl. No.: 15/653,657

(22) Filed: Jul. 19, 2017

(65) Prior Publication Data
US 2017/0312103 A1 Nov. 2, 2017

Related U.S. Application Data

(63) Continuation of application No. PCT/US2016/012913, filed on Jan. 11, 2016.
(Continued)

(51) Int. Cl.
*A61F 2/07* (2013.01)
*A61F 2/856* (2013.01)
(Continued)

(52) U.S. Cl.
CPC .......... *A61F 2/856* (2013.01); *A61F 2/07* (2013.01); *A61F 2/89* (2013.01); *A61F 2002/068* (2013.01); *A61F 2002/823* (2013.01)

(58) Field of Classification Search
CPC ...... A61F 2/89; A61F 2/90; A61F 2/95; A61F 2002/9522; A61F 2/93; A61F 2/06;
(Continued)

(56) References Cited

U.S. PATENT DOCUMENTS

| 6,258,117 B1 * | 7/2001 | Camrud | A61F 2/82 623/1.16 |
| 2006/0122694 A1 * | 6/2006 | Stinson | A61F 2/91 623/1.34 |

(Continued)

FOREIGN PATENT DOCUMENTS

| CN | 101045022 B | 8/2010 |
| CN | 102499802 A | 6/2012 |

(Continued)

OTHER PUBLICATIONS

EPO, Extended European Search Report in European Patent Application No. 16743828.2 dated Sep. 25, 2018.
(Continued)

*Primary Examiner* — Alvin J Stewart
(74) *Attorney, Agent, or Firm* — NK Patent Law

(57) ABSTRACT

A device for placement in the aortic arch of a patient is provided. The device includes a distal portion for being engageably received in an aortic arch of a patient beyond the left subclavian artery and a stent portion fluidly engaged with the distal portion, the stent portion being permeable and configured to span a portion of the aortic arches to which the brachiocephalic trunk, left common carotid artery, and left subclavian artery attach to the aortic arch. A diameter of the stent portion may be modified by translation of the proximal portion to thereby alter a length of the stent portion thus causing modification of the diameter of the stent portion to fit anatomical features of differing dimensions.

11 Claims, 18 Drawing Sheets

Related U.S. Application Data

(60) Provisional application No. 62/108,563, filed on Jan. 28, 2015.

(51) Int. Cl.
    *A61F 2/89*     (2013.01)
    *A61F 2/06*     (2013.01)
    *A61F 2/82*     (2013.01)

(58) Field of Classification Search
    CPC .. A61F 2/915; A61F 2/856; A61F 2/07; A61F 2/86; A61F 2/966; A61F 2/848; A61F 2/852; A61F 2/92; A61F 2002/9505; A61F 2/9511; A61F 2002/9528; A61F 2002/9534; A61F 2/954
    See application file for complete search history.

(56) References Cited

U.S. PATENT DOCUMENTS

2007/0168013 A1    7/2007   Douglas
2013/0144373 A1    6/2013   Shahriari
2014/0172064 A1    6/2014   Kelly
2014/0214051 A1    7/2014   Bolduc
2014/0316513 A1   10/2014   Tang

FOREIGN PATENT DOCUMENTS

| | | |
|---|---|---|
| CN | 103209660 A | 7/2013 |
| CN | 203107339 U | 8/2013 |
| WO | 2004103217 A1 | 12/2004 |
| WO | 2014141232 A1 | 9/2014 |

OTHER PUBLICATIONS

PCT, International Search Report for International Patent Application No. PCT/US2016/012913 dated May 19, 2016.

CNIPA, Notification of Second Office Action for Chinese Application No. 201680007062.2, dated Jul. 18, 2019.

* cited by examiner

US 10,478,320 B2

MODULAR ENDO-AORTIC DEVICE FOR ENDOVASCULAR AORTIC REPAIR OF DISSECTIONS AND BEING CONFIGURED FOR ADAPTABILITY OF ORGANS OF VARIOUS ANATOMICAL CHARACTERISTICS AND METHOD OF USING THE SAME

CROSS-REFERENCE TO RELATED APPLICATIONS

This application claims priority to Patent Cooperation Treaty Application No. PCT/US16/12913 filed on Jan. 11, 2016, which claims priority to U.S. Provisional Patent Application No. 62/108,563 filed on Jan. 28, 2015, the entire contents of both of which are incorporated by reference herein.

TECHNICAL FIELD

The present disclosure relates to a modular device and method of using the same for endovascular aortic repair, including repair of aortic valve disease, aortic stenosis, ascending aortic aneurysms, aortic insufficiency, aortic regurgitation, ascending aneurysm, bicuspid valve disease, and/or aortic dissections.

BACKGROUND

Aortic dissections are life threatening conditions that start with a tear in the aorta. Over 70% occur in the ascending aorta and arch. An aortic dissection develops when a small tear in the intima of the vessel allows blood to penetrate between the intima and the media/adventitia of the aorta thereby separating the layers of the aorta. This creates two lumens within the aorta, the false (FL) and the true (TL) lumens. This separation causes entry of the pulse pressure which in turn will cause propagation of the tear until a re-entry point is created equalizing the pressure in the FL and TL. The short and long-term consequences of the dissection can be disastrous. In short term, they can cause strokes, ruptures, and malperfusion to branch vessels with deadly consequences. In fact, the 72 hour mortality for untreated type A dissections is approximately 75%. Long-term consequences include degeneration into chronic dissection, re-dissection, and aneurysm formation. These are all very difficult to treat consequences. The principles of treating dissections today entail a) removing or covering the initial intimal tear and b) an attempt to close the FL by tacking the intima to the rest of the wall of the aorta. Removal/coverage of the site of the tear is done effectively by surgically removing and replacing the area of the tear or to cover the tear with an endograft. However, current techniques to tack the intima and close the FL are ineffective and inadequate. In this document, we disclose inventions for transcatheter treatment of dissections with the principles of covering the tear and tacking the intima as basis.

Additionally, the aortic arch of a patient may have variation in size, dimensions and the like. Use of stent portions for being received within the arch are thus constrained by the variations among different aortic arches.

There are devices clinically used for endovascular repair of ascending aortic aneurysms. Although transcatheter valves are a clinical reality, none in clinical use have been designed with the purpose of endovascular repair of multiple types of ascending aortic aneurysms or dissections. Indeed, a device is needed that can treat different anatomical variations of ascending aortic aneurysms and dissections, create effective proximal and distal seal zones within the aorta, and have a durable valve component, but that also allows for future valve re-interventions. A device is also needed that would allow for treatment of different coronary anatomical variations among the patient population, allow future coronary re-intervention, but that also avoids coronary compression, and enables treatment of possible paravalvular leaks.

SUMMARY

According to one aspect of the disclosure, a device for placement in the aortic arch of a patient is provided. The device includes a proximal impermeable portion supported by stents, engaging the ascending aorta proximal to the innominate trunk fluidly engaged with a stent portion that is permeable and configured to span a portion of the aortic arches to which the brachiocephalic trunk, left common carotid artery, and left subclavian artery attach to the aortic arch. The device also includes a distal portion for being engageably received in an aortic arch of a patient beyond the left subclavian artery and a stent portion fluidly engaged with the distal portion, the stent portion being permeable and configured to span a portion of the aortic arches to which the brachiocephalic trunk, left common carotid artery, and left subclavian artery attach to the aortic arch. A diameter of the stent portion may be modified by translation of the proximal portion or distal portion to thereby alter a length of the stent portion thus causing modification of the diameter of the stent portion.

According to one or more embodiments, the proximal portion is impermeable.

According to one or more embodiments, the distal portion is impermeable.

According to one or more embodiments, the proximal portion is configured to receive a transcatheter stent valve.

According to one or more embodiments, the distal portion is configured to receive one or more stent members.

According to one or more embodiments, the device includes one or more stent members extending from the proximal portion.

According to one or more embodiments, a kit is provided. The kit includes a device for placement in the aortic arch of a patient. The device includes a distal portion comprising a graft encompassing a stent for being engageably received in an aortic arch of a patient beyond the left subclavian artery, a stent portion fluidly engaged with the distal portion, the stent portion being permeable and configured to span a portion of the aortic arches to which the brachiocephalic trunk, left common carotid artery, and left subclavian artery attached to the aortic arch, and a proximal portion comprising a graft encompassing stent support members configured for being slideably received within the stent portion on one end and into a stent assembly in the ascending aorta on another end. A diameter of the stent portion may be modified by translation of the proximal portion or distal portion to thereby alter a length of the stent portion thus causing modification of the diameter of the stent portion. The kit further includes a deployment apparatus comprising a sheath and a tip for housing the device and having a wire passing through a center therethrough for deploying the device at an operational site.

According to one or more embodiments, the kit includes a stent device for placement in the aorta of a patient. A diameter of the stent device may be modified by translation of an end of the stent device to thereby alter a length thereof causing modification of the diameter of the stent device. A deployment apparatus includes a sheath for housing the stent device and having a guide rod passing through a center therethrough for deploying the stent device at an operational site. The sheath constrains the stent in a compressed state and the guide rod carrying the stent device and being removable through a center of the stent when the stent is in an expanded state upon removal of the sheath.

According to one or more embodiments, the stent device includes at least one eyelet on a first end facing an operator, and the deployment apparatus further includes a pawl that is configured to engage the eyelet to expand and contract the end of the stent device to thereby shorten and elongate the stent device.

According to one or more embodiments, the pawl is initially retracted to contract the end of the stent device.

According to one or more embodiments, the pawl is initially retracted by a sleeve extending thereabout and the sleeve is translatable away from the pawl to thereby expand the pawl.

According to one or more embodiments, the pawl and the sleeve are translatable relative to the guide rod to alter one or more dimensions of the stent device.

According to one or more embodiments, the deployment device includes a guide wire extending through the guide rod and through a bumper on a second end opposed to the operator.

According to one or more embodiments, a portion of the stent device proximal the second end is covered with graft material.

According to one or more embodiments, the portion of the stent device covered with graft material includes a supporting wire frame.

According to one or more embodiments, a portion of the stent device proximal the first end is covered with graft material.

According to one or more embodiments, the portion of the stent device covered with graft material includes a supporting wire frame.

According to one or more embodiments, the second end is telescopically engaged with a prosthetic device engaged in an adjacent anatomical organ.

According to one or more embodiments, the guide rod has a major external diameter that is about equal to an interior diameter of the stent device in the compressed state.

According to one or more embodiments, a method includes extending a stent device engaged with a guide rod and having a constraining sheath thereabout into a patient's aorta and expanding a first end of the stent device by translating the sheath such that at least a portion of the stent is uncovered to thereby engage the first end of the stent with the aorta. At least a portion of the stent device is uncovered to span one or more arteries fluidly coupled to the aorta. The method includes expanding a remainder of the stent device by translating a pawl about the guide rod through a handle component to expand or retract the stent device to adjust its length, diameter and wall apposition to engage the remainder with the patient's aorta.

According to one or more embodiments, extending the stent device into the patient's aorta includes extending the first end into an ascending portion of the aorta and a second end into a descending portion of the aorta. Upon expanding the first end, the first end is engaged with the ascending portion of the aorta and the uncovered portion of the stent expands the aortic arch and its branches.

According to one or more embodiments, extending the stent device into the patient's aorta comprises extending the first end into a descending portion of the aorta and a second end into an abdominal portion of the aorta. Upon expanding the first end, the first end is engaged with the descending portion of the aorta and the uncovered portion of the stent expands the abdominal aorta and its visceral branches.

According to one or more embodiments, the one or more arteries are aortic arch branch arteries that include the brachiocephalic trunk, left common carotid artery, and left subclavian artery.

According to one or more embodiments, the one or more arteries are abdominal visceral branch arteries that include the celiac trunk, superior mesenteric artery, and the renal arteries.

According to one or more embodiments, adjustable expansion of the uncovered portion of the stent device allows reattachment of the intimal flap of an aortic dissection and fusing the intimal flap to the remainder of the aortic wall.

According to one or more embodiments, the second end can be translated within the aorta by manipulation of a tool engaged therewith in order to elongate or shorten the stent. Thus, the stent increases in a diameter thereof during shortening and decreases in diameter thereof during lengthening.

According to one or more embodiments, the method includes engaging the first end of the stent device with a transcatheter stent valve.

According to one or more embodiments, the first end is engaged within the transcatheter stent valve to define a total length of the stent device and transcatheter stent valve.

According to one or more embodiments, the first end is telescopically engaged with the transcatheter stent valve to define a total length of the stent device and transcatheter stent valve.

According to one or more embodiments, the method includes telescopically engaging the first end of the stent device with an endograft in an ascending portion of the aorta.

According to one or more embodiments, the first end is telescopically engaged with the endograft to define a total length of the stent device and endograft.

According to one or more embodiments, the method includes engaging the first end of the stent device with an endograft in a thoracic aorta.

According to one or more embodiments, the first end is telescopically engaged with the endograft to define a total length of the stent device and endograft.

According to one or more embodiments, the method includes telescopically engaging the first end of the stent device with an endograft in an abdominal aorta.

According to one or more embodiments, the first end is telescopically engaged with the endograft to define a total length of the stent device and endograft.

According to one or more embodiments, a deployment apparatus is provided and includes a sheath for housing a stent device and having a guide rod passing through a center therethrough for deploying the stent device at an operational site. The sheath constrains the stent in a compressed state and the guide rod carrying the stent device and is removable through a center of the stent when the stent is in an expanded state upon removal of the sheath. A pawl is configured to engage an end of the stent device to expand and contract the end of the stent device to thereby shorten and elongate the stent device.

A method is provided that includes extending a stent device engaged with a guide rod into a patient's aorta and expanding a first end of the stent device such that at least a portion of the stent is uncovered to thereby engage the first end of the stent with the aorta. At least a portion of the stent device is uncovered to span one or more arteries fluidly coupled to the aorta. The method includes partially expanding a remainder of the stent device while pushing a deployment apparatus engaged therewith to reduce the length and increase the diameter of the stent device until the stent device is in a desired operational position at which the stent device is then fully expanded into engagement with the aorta.

According to one or more embodiments, the stent device is fully expanded by releasing an end of the stent device that is engaged through an eyelet of the stent device with a pawl.

According to one or more embodiments, a prosthetic assembly is provided that includes a stent device for placement in the aorta of a patient. A diameter of the stent device may be modified by translation of an end of the stent device to thereby alter a length thereof causing modification of the diameter of the stent device. The assembly includes a prosthetic in telescopic engagement with the stent device. The stent device is deployed by translating a sheath constraining the stent device until the stent is partially expanded and in engagement with an aorta.

According to one or more embodiments, the prosthetic is a stent valve.

BRIEF DESCRIPTION OF THE DRAWINGS

Embodiments of the present disclosure will now be described by way of example in greater detail with reference to the attached figures, in which.

DETAILED DESCRIPTION OF THE DRAWINGS

Figure 1:
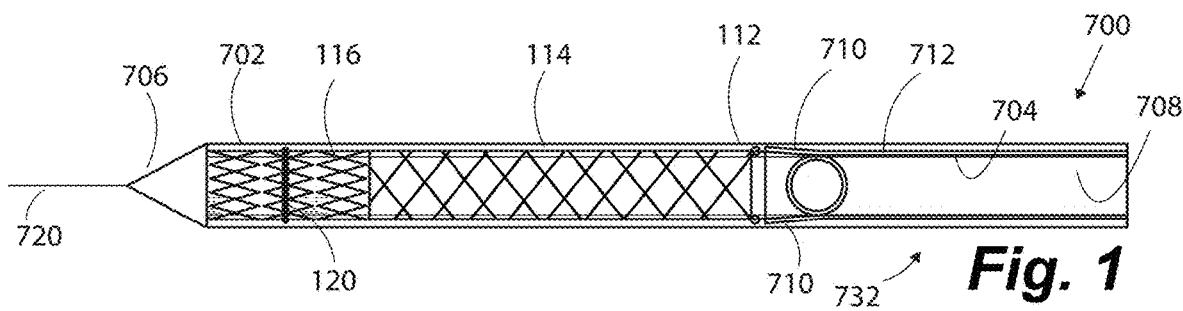
FIG. 1 is a side view of a kit that includes a stent and a deployment device according to one or more embodiments disclosed herein.

While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, distal, proximal, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. For example, the term "proximal" refers to the direction that is generally closest to the heart, and the term "distal" refers to the direction that is generally furthest from the heart.

A kit is provided and generally designated 10 and is provided for repairing one or more anatomical defects in an aorta, where the kit is particularly suited for conforming to aortas of various anatomical sizes and characteristics. The kit 10 includes a stent device for placement in the aortic arch of a patient is generally designated 110. The stent device 110 includes a distal portion or first end portion 112 for being engageably received in an aortic arch of a patient beyond the left subclavian artery in an embodiment where deployed in the aortic arch. The distal portion 112 may be impermeable and include a polyester, PTFE, or other biological compatible blood impermeable material covering, or the distal portion 112 may not include a covering at all and instead define an exposed wire frame. A stent frame such as a continuous wire stent frame or one created of multiple wires may be provided and form the stent device 110. In addition the stent frame may be laser cut and in a gridded pattern. The distal portion 112 may also be referred to herein as a graft portion in embodiments where the distal portion includes a covering.

A stent portion 114 may be fluidly engaged with the distal portion 112. The stent portion 114 may be permeable and configured to span a portion of the aortic arches to which the brachiocephalic trunk 2, left common carotid artery 3, and left subclavian artery 4 attach to the aortic arch 1. In this manner, blood flow to each of the brachiocephalic trunk 2, left common carotid artery 3, and left subclavian artery 4 flows uninhibitedly through the stent portion 114. The distal portion 112 may be attached to the stent portion 114 by another layer of graft material. The stent portion 114 may be a braided stent as illustrated. The stent portion may also be non-braided laser cut with a gridded pattern.

A proximal portion 116 is configured for being engaged with the stent portion 114 on one end and into the aorta proper or a stent device in the aorta 1 on another end. The proximal portion may have a diameter larger than 10 mm. The proximal portion 116 may be configured for engaging with device 110. The proximal portion 116 may be impermeable and include a polyester, PTFE, or other biological compatible blood impermeable material covering.

As discussed in this document, a diameter of the stent portion 114 may be modified by translation of either of the distal portion 112 or the proximal portion 116 to thereby alter a length of the stent portion 114 thus causing modification of the diameter of the stent portion. In other words, the stent portion 114 is capable of changing diameter based on the forces it is exposed to that will lengthen or shorten it. For example, the stent portion 114 may have a relaxed diameter of 55 mm when the length of the stent portion is also 50 mm. If the stent portion 114 is stretched to 80 mm, the diameter of the stent portion 114 is then reduced to 30 mm. This is useful for treatment of various aortas with different diameters.

A deployment apparatus is generally designated 70. The deployment apparatus 70 includes a sheath 702 that expands circumferentially over the deployment apparatus 710 and the stent device 110. The sheath 702 is thus provided for housing the stent device 110. The sheath 702 is configured for constraining the stent device 110 in a compressed state when the sheath 702 is positioned over the stent device 110. The sheath 702 is retractable by pulling towards the operator. As the sheath 702 is retracted, the now exposed portions of the stent device 110 begin to expand outwardly. For example, in FIG. 2, the sheath 702 is shown fully retracted and the stent device 110 is expanded outwardly. A slip joint or other constraining device 120 may be provided along portion 116 for radially constraining that portion until removal of the constraining device 702. A guide rod 708 passes through a center of the deployment apparatus 700 and into engagement with the compressed stent device 110 shown in FIG. 1. In this manner, extension of the guide rod 708 imparts a corresponding translation of the stent device 110. The stent device 110 is configured such that the guide rod 708 provides an engagement surface for the stent device 110 when in the compressed state. In this manner, in one or more embodiments, an outer diameter of the guide rod 708 is about equal to an inner diameter of the stent device 110 when in a compressed state.

Figure 2:
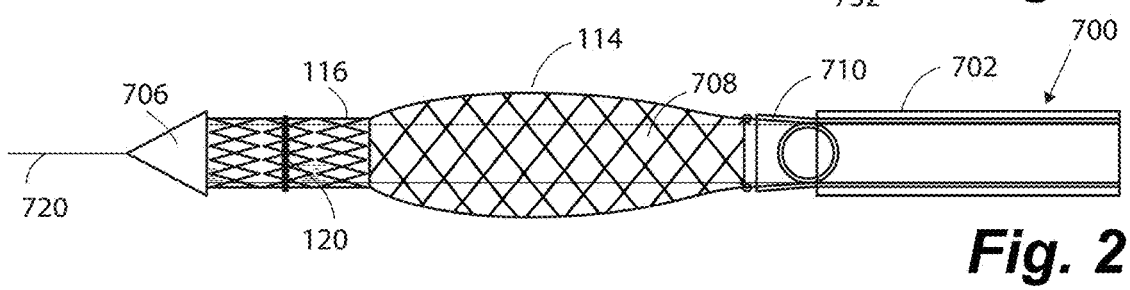
FIG. 2 is a sequential side view of the kit of FIG. 1 in which a medial portion of the stent has been at least partially expanded according to one or more embodiments disclosed herein.
Figure 3:
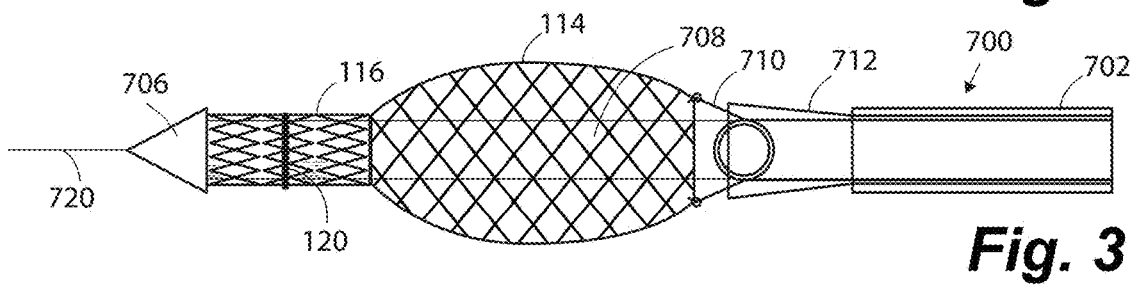
FIG. 3 is a sequential side view of the kit of FIG. 2 in which a medial portion of the stent has been more expanded according to one or more embodiments disclosed herein.
Figure 4:
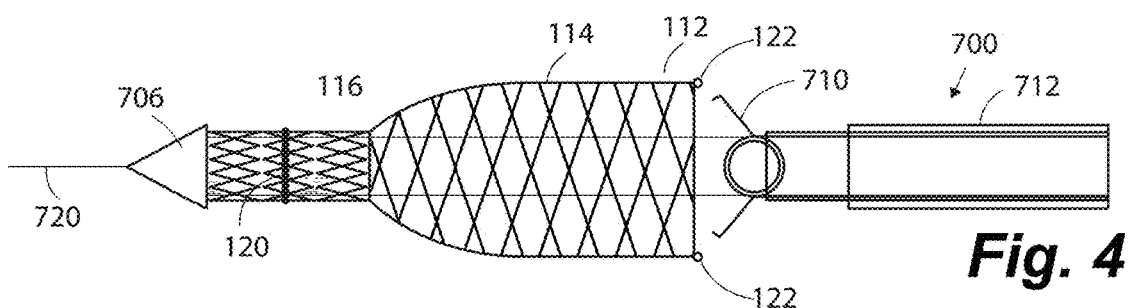
FIG. 4 is a sequential side view of the kit of FIG. 3 in which a medial portion of the stent has been more expanded and an end close to the deployment device has been released and expanded according to one or more embodiments disclosed herein.

Upon partial expansion of the stent device 110, mainly medial portion 114 as illustrated in FIG. 2, a pawl 710 configured to engage an eyelet 122 on the stent device 110 is released outwardly, causing further radial expansion of the stent device 110 as illustrated in FIG. 3 and FIG. 4, where FIG. 4 shows the stent device 110 being disengaged from the pawls 710.

Figure 5:
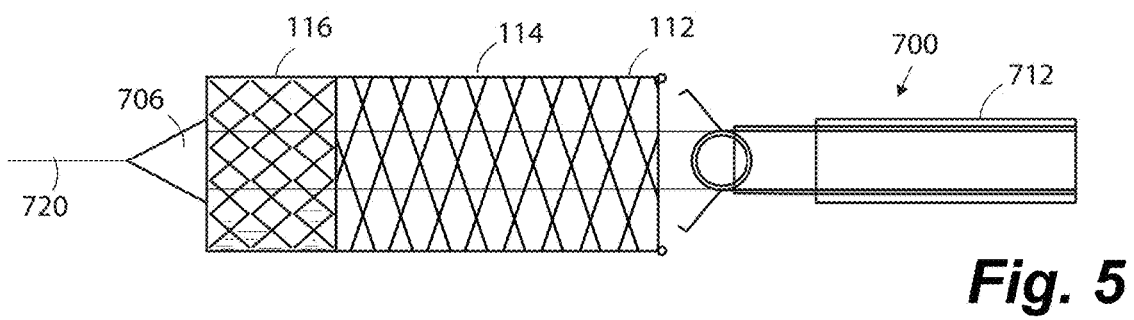
FIG. 5 is sequential side view of the kit of FIG. 4 where an end furthest from the deployment device has been released and expanded according to one or more embodiments disclosed herein. In this illustration, the proximal end is shown as transparent in order to provide illustration of the guide rod, however, in embodiments where the proximal end is covered, the guide rod may not be visible in these sections.
Figure 6:
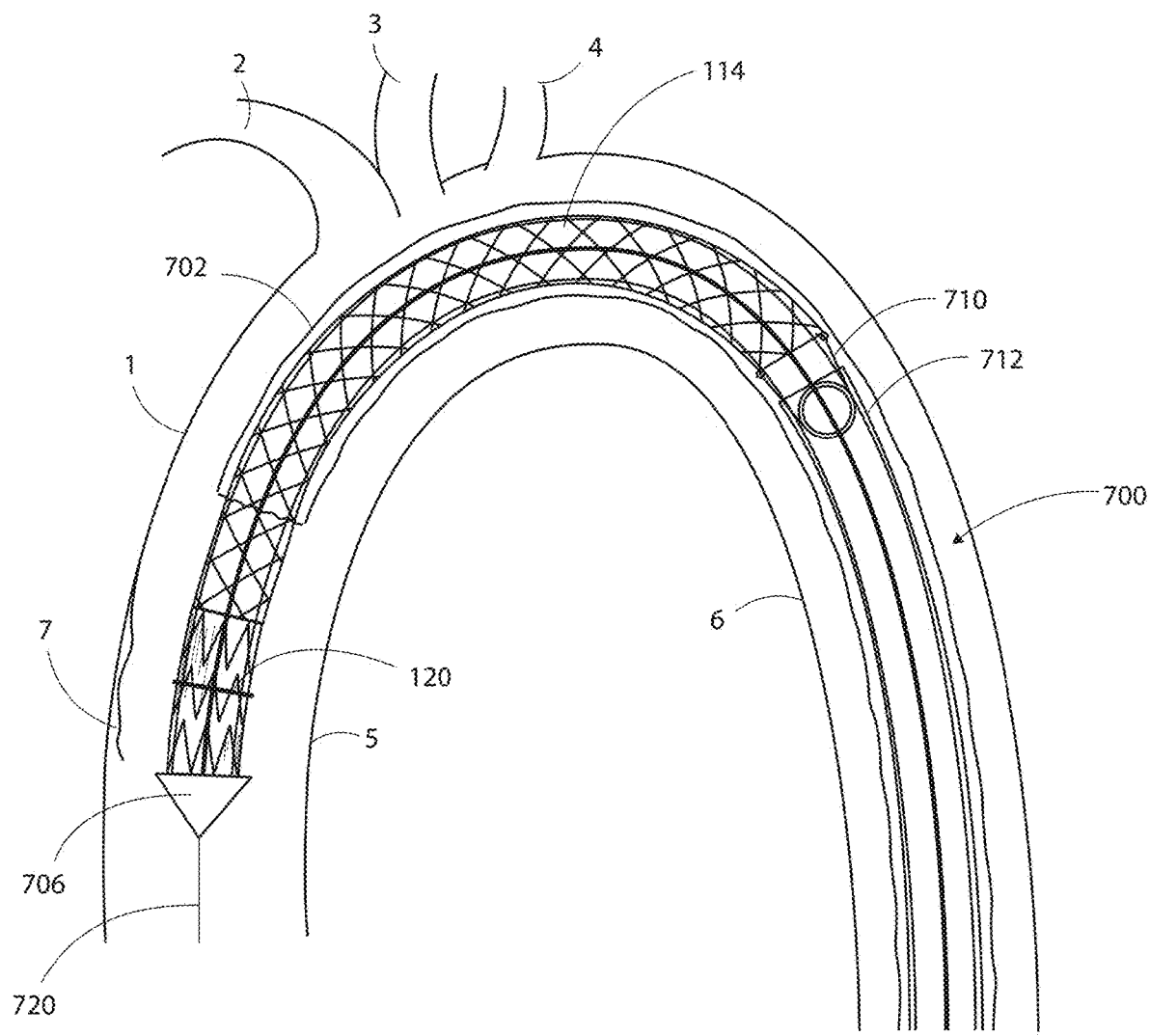
FIG. 6 is a view of an aorta with the stent and deployment device being positioned within an aorta according to one or more embodiments disclosed herein.

In one or more embodiments, pawls 710 are operated by translation of a sleeve 712, which is removed from interference with pawls 710 in FIGS. 4 and 5. Upon removal, the pawls 710 are biased outwardly and bias out of engagement with eyelets 122. The pawls can be contracted back inwardly by translation of the sleeve 712 towards the stent device 110 if desired.

The portion 116 is finally expanded by removal of constraining member 120. This constraining member may be removed by manipulation of a rip cord or the like according to one or more embodiments disclosed herein.

The deployment device 700 further includes a tipped end 706 that has a major dimension at least equal to the outer circumference of the stent 110 when in a compressed state. In this manner, the tipped end 706 provides for guidance characteristics while manipulating the stent device 110 and deployment apparatus 710 within the aorta and further provides for blocking further movement of the stent device 110 in a longitudinal direction relative to the guide rod 708.

Extending through the tipped end 706 may be provided a guide wire 720 that provides further guidance characteristics while manipulating the stent device 110 and deployment apparatus 710 within the aorta. The guide wire 720 may be extended through the tipped end 706 and guide rod 708 and may be manipulated by the operator.

After full expansion of the stent device 110 as illustrated in FIG. 5, the guide rod 708 may be retracted away from the deployed stent device 110 and out of the aorta. This will impart similar movement to the tipped end 706.

While the embodiments illustrated show an enlarged diameter stent frame when in the relaxed state, the devices disclosed herein could also have a relatively reduced diameter stent frame when in the relaxed state, where the diameter is increased by shortening the overall length of the device 110.

A type A dissection 7 is shown in FIGS. 6 through 10 illustrate application of the stent device 110 in the aorta during the repair of an aortic dissection. The kit 10, including the device 110 and deployment device 710, is deployed in the diseased sections, in these cases covering the supra-aortic and visceral aortic branches. The proximal part (where proximal designates the portion further from the operator, but installed in the ascending portion of the aorta) of the device 110 is inserted with the deployment device 710. The insertion may be performed through a groin or other insertion point in the human anatomy.

Once the uncovered portion is deployed, the portion 116 may be pushed proximally or pulled distally to adjust the diameter of the uncovered stent device 110. In this fashion, the uncovered stent device 110 will tack the dissection flap 7 against the media and the adventitial layers of the aortic wall and promote healing. The stent portion 114 may be axially translatable on the guide rod 708 of the deployment apparatus 700 relative to the portion 116 allowing the stent portion 114 to shorten and elongate, thereby increasing or reducing its diameter to create apposition with the aortic wall and re-attach the intimal flap. Once the stent portion 114 is in good apposition with the aortic wall, the proximal portion 116 of the device is deployed followed by the distal portion 112, or the distal portion 112 is deployed and then followed by the proximal portion 116.

As illustrated, the stent device 110 is deployed in the aortic arch such that the braided, uncovered stent portion 114 spans the aortic arch including the brachiocephalic trunk 2, left common carotid artery 3, and left subclavian artery 4.

Figure 7:
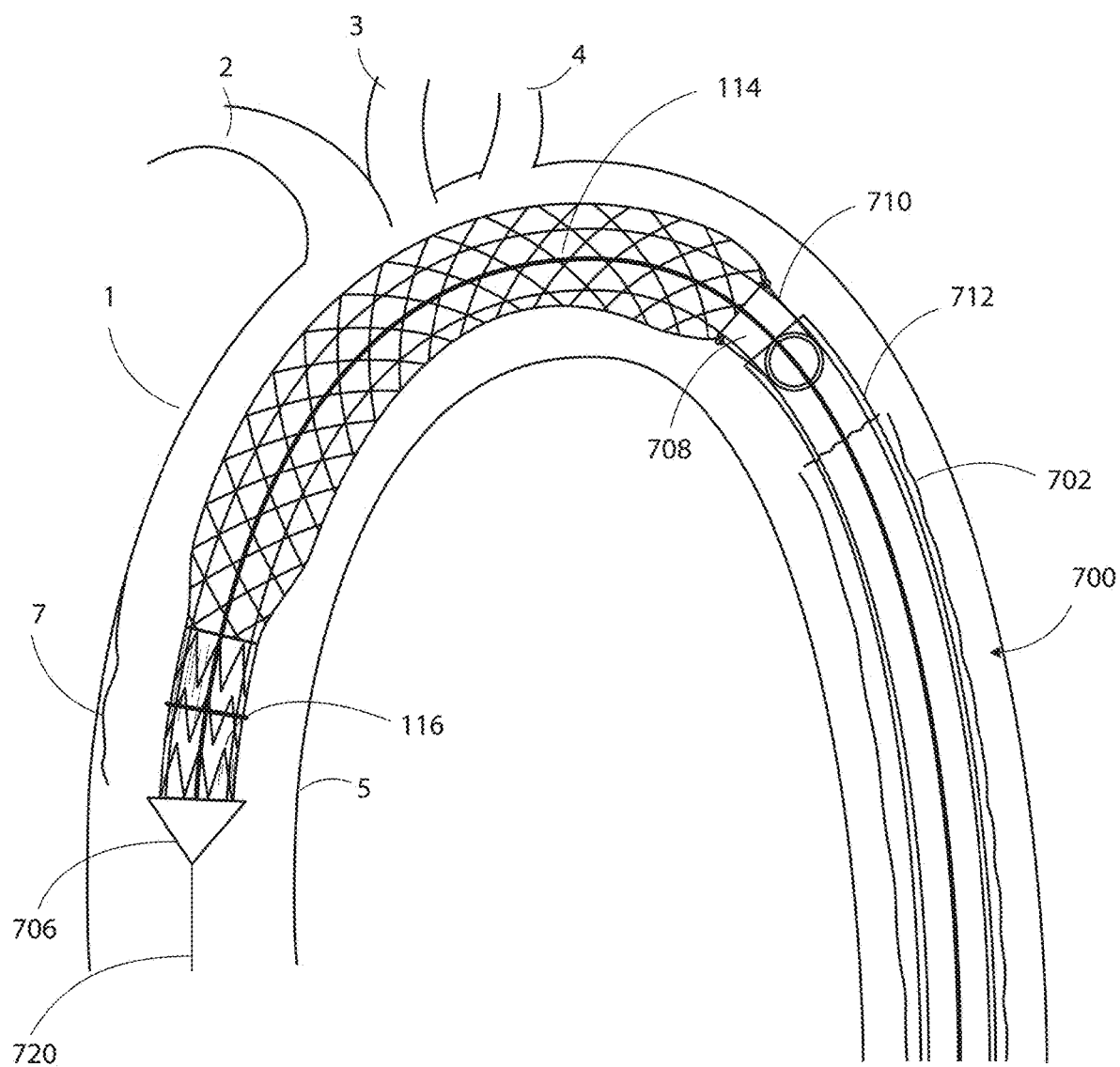
FIG. 7 is a sequential side view of an aorta with the stent and deployment device being positioned within an aorta, where the stent is partially expanded relative to the stent in FIG. 6 according to one or more embodiments disclosed herein.
Figure 8:
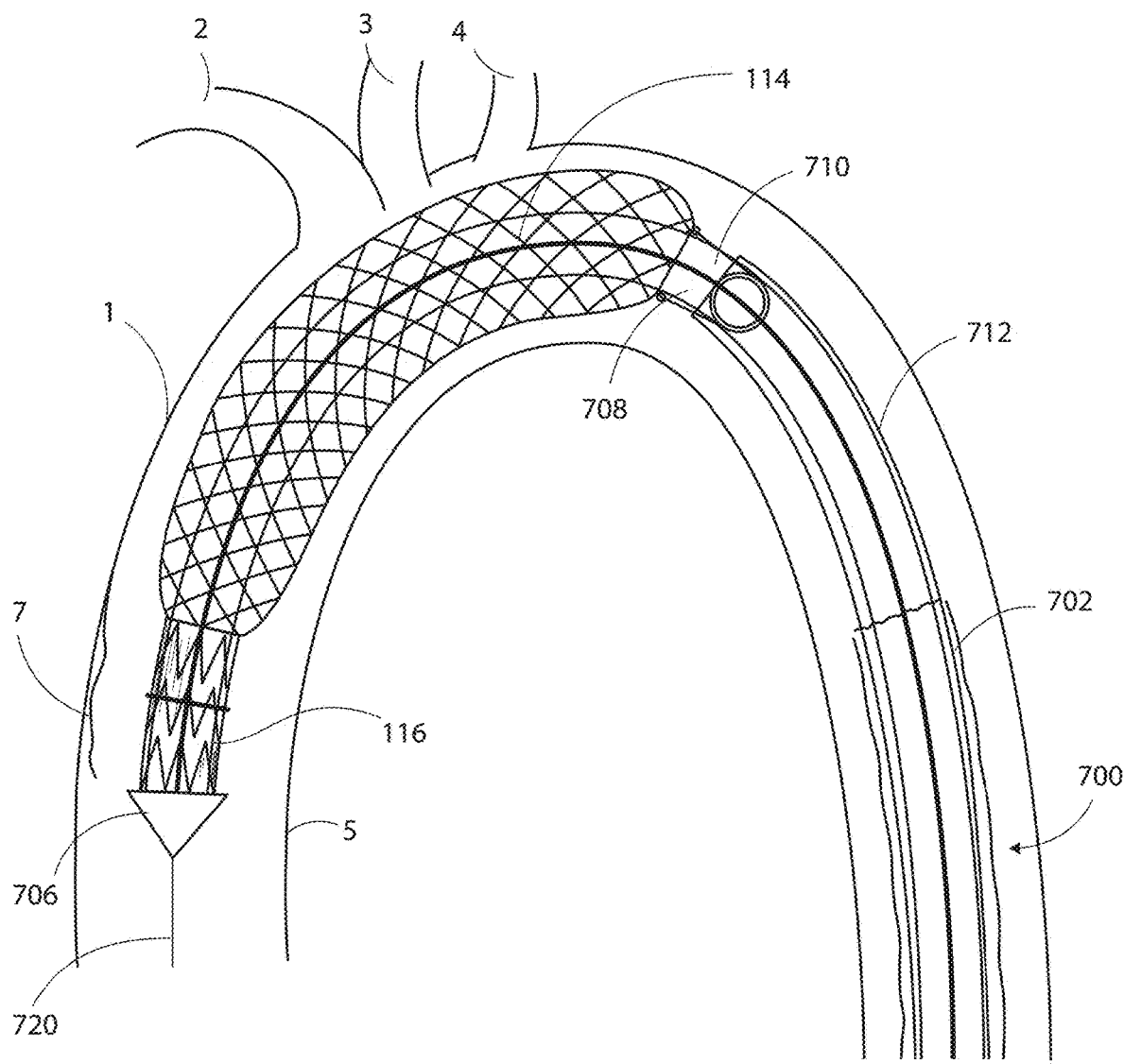
FIG. 8 is a sequential side view of an aorta with the stent and deployment device being positioned within an aorta, where the stent is partially expanded relative to the stent in FIG. 7 according to one or more embodiments disclosed herein.
Figure 9:
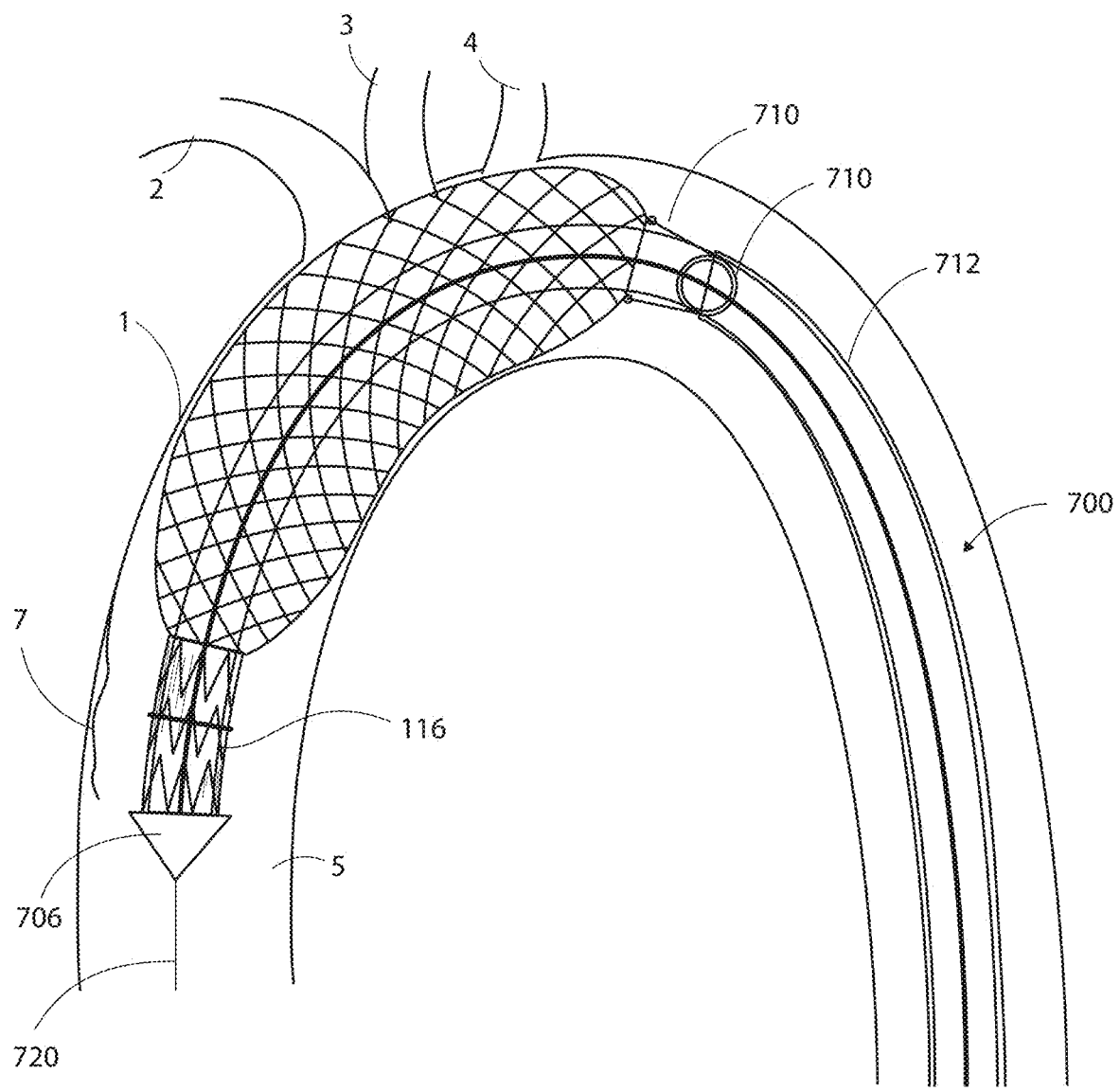
FIG. 9 is a sequential side view of an aorta with the stent and deployment device being positioned within an aorta, where a medial portion of the stent is fully expanded into engagement with the aorta according to one or more embodiments disclosed herein.
Figure 10:
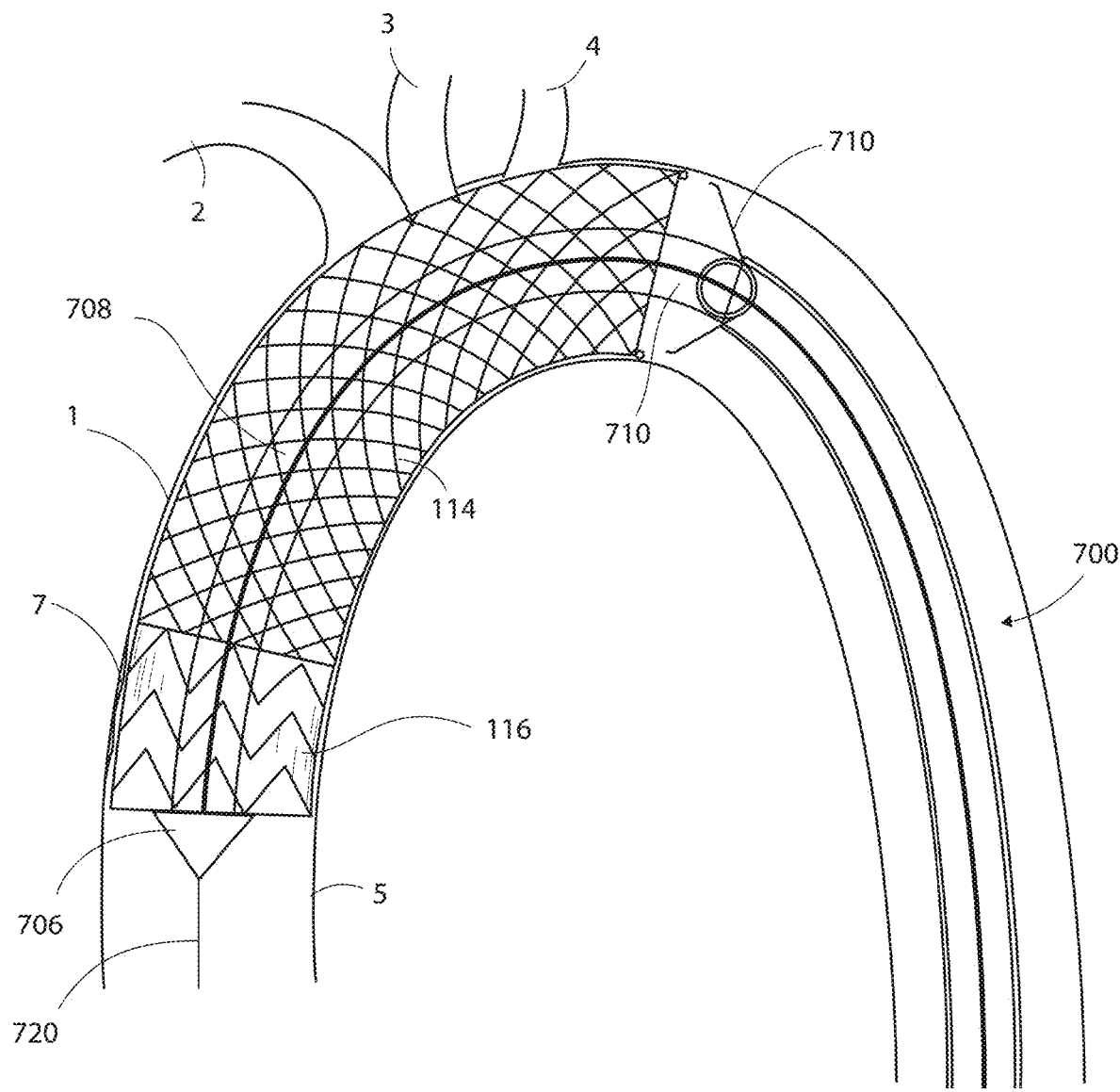
FIG. 10 is a sequential side view of an aorta with the stent being fully expanded into engagement with an aorta according to one or more embodiments disclosed herein.
Figure 11:
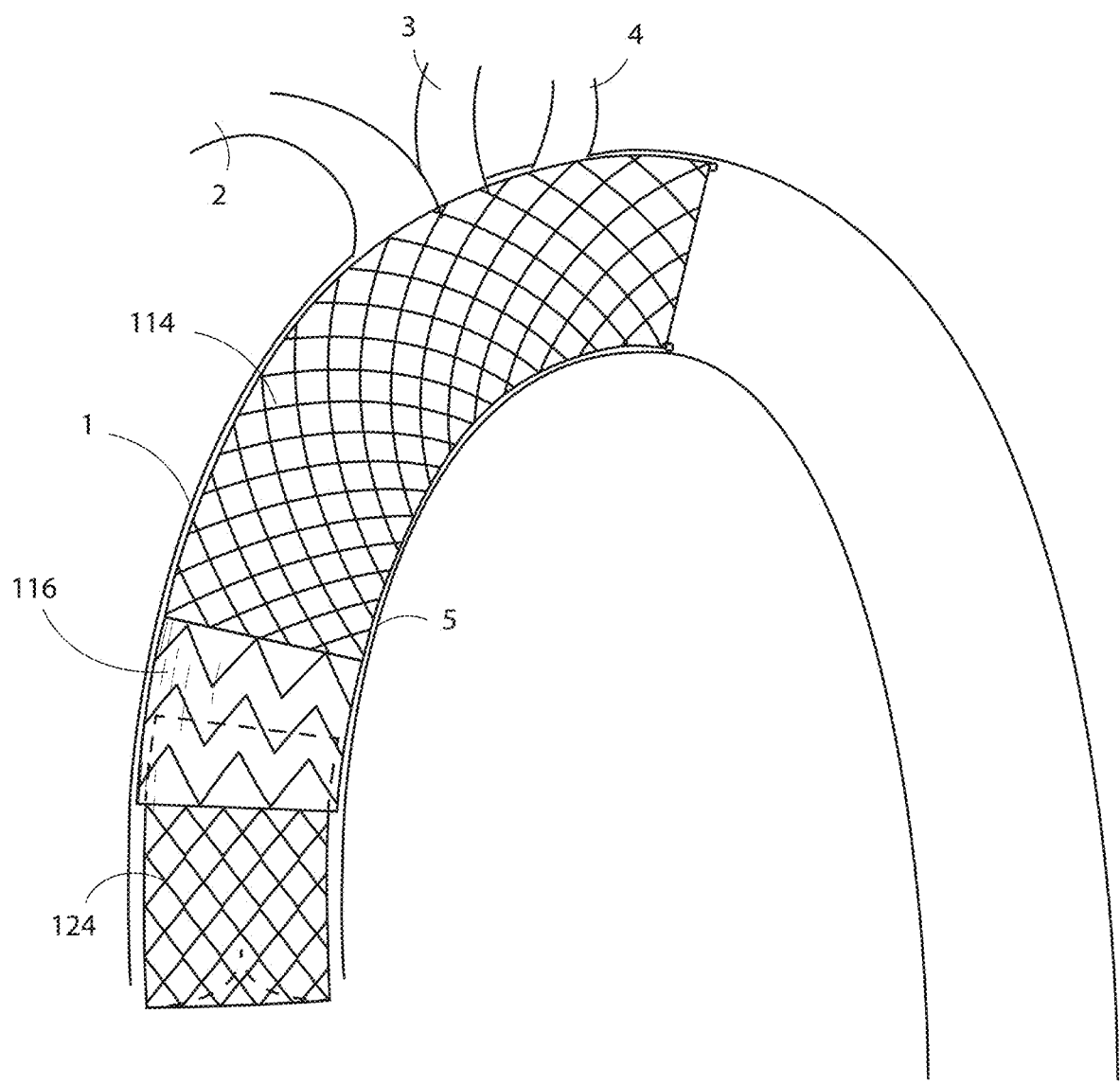
FIG. 11 is a view of the stent being engaged with a prosthetic in the aorta according to one or more embodiments disclosed herein, where the prosthetic is shown as a trancatheter stent valve in the illustrated embodiment.

As the diameter of the uncovered braided stent device 110 is dependent on the pull/push forces applied to it, during the deployment of the stent component 110 the surgeon can push on the deployment device 700 to increase the diameter of the braided stent 110 or pull the deployment device 700 while it is still engaged with the eyelets 112 to stretch and reduce the diameter of the braided stent. This property allows the stent device 110 to conform itself to the diameter of the aorta. As illustrated in FIG. 6 through FIG. 11, the kit 10 is deployed within the aorta. The sleeve 712 is then pulled back, releasing the medial portion 114 to expand outwardly as illustrated in FIG. 7. At this time, if the operator choses, they may push on the deployment device 700 to enlarge the diameter of the stent device 110 or pull on the deployment device 700 to decrease the diameter of the stent device 110. The sleeve 712 is then pulled back, allow pawls 710 to bias outwardly, thus causing outward and radial expansion of portion 112. This is illustrated in FIG. 9 where the deployment device 700 is being pushed while the sleeve 712 is pulled backward to allow outward expansion of pawls 710. In this illustration, all but portion 116 of the stent device 110 begins to seat against the aorta. Portion 116 is then released by release of the constraining member 120, to fully expand the stent device 110 into engagement and deployment. The deployment apparatus 700 is then retracted.

Stent device 110 may be engaged with a prosthetic component 124, where the stent device 110 is telescopically engageable with the prosthetic component 124. In this manner, a total length of stent device 110 and prosthetic 124 may be defined by the telescopic engagement of both components. In this manner, the devices, systems, and kits disclosed herein provide for modularity in both length of devices being deployed and diameter and other characteristics. Prosthetic 124 may be a transcatheter valve, as shown with the dashed lines indicating the valve, or similar.

In yet another embodiment, a protrusion is placed on the inner core of the delivery device which is used to stabilize the proximal portion 116 of the endograft implant onto the inner rod once the implant is loaded. Slip joints using Tevdek or other biocompatible suture materials are used to constrain the proximal component 116 to the protrusion. Together the protrusion and the slip joints stabilize component 116 onto the guide rod 708 and allow for controlled expansion of this component. The terminal end of the suture material is passed through the guide rod 708 to exit the handle component of the delivery device where it is secured in place by a terminal cap. The stent component of the implant is stretched over the inner core to reduce its profile and pack the stent within the sheath. The distal most portion of the stent component 114 or the implant 112 may be equipped with eyelets that engage a clasping mechanism. The clasping mechanism is attached to a metal rod that is axially translatable along the inner core with its terminal end positioned in the handle component in such a way that the operator can axially pull or push the clasping mechanism. Once the assembly has been introduced into the aorta and reached the desired location the implant is exposed by unsheathing the delivery system. At this stage the operator may choose to expand the proximal component 116 first by pulling on the cap and unraveling the slip joints constraining the proximal graft component 116. Alternatively the proximal component 116 may be expanded after the uncovered stent portion 114 is deployed. To fully expand and deploy the uncovered stent component 114, the clasping mechanism and its connecting rod are used and the operator can push or pull on the clasping mechanism to shorten or elongate the stent component 114 thereby increasing or reducing the diameter of the stent until perfect apposition to the aortic wall is achieved. At this point the clasping mechanism is released and the implant is fully released from the delivery system.

The pawls 710 are attached to the connecting rod 730 that exits the handle component 732. Sliding axially over the connecting rod 730 is the sheath 702 that engages the pawls 710 externally. By moving the sheath 702 over the pawls 710, the pawls 710 will clamp down and firmly hold the stent eyelets 12. Once the sheath 702 is pulled back the pawls 710 release the eyelets 122. Thus, during the loading process onto the implant the stent eyelets 122 are engaged by the pawls 710 and the sheath 702 is pushed over the pawls 710 so they can hold and control the movements of the stent device 110 by the operator. Once the sheath 702 is positioned over the pawls 710 it can be secured in position by a screw mechanism in the handle component 732 allowing the entire pawl mechanism to move axially as a unit. Once the stent device 110 has reached the desired location in the aorta and the delivery device 700 is unsheathed, the inner core and guide rod 708 of the delivery system 700 is held steady thereby stabilizing the position of the stent component 116. The clasping mechanism is now moved axially and the diameter and length of the uncovered stent component 114 is optimized and adjusted until adequate apposition to the aortic wall has been achieved. The sleeve 702 is now released by unscrewing the handle component moving the sleeve 702 to release the pawls 710 which now will disengage the distal stent eyelets 122 allowing the expansion of stent component 114. The proximal stent component 116 is either deployed immediately prior to or following the release of the uncovered stent 114 by releasing the cap and unraveling the slip joints.

Figure 12:
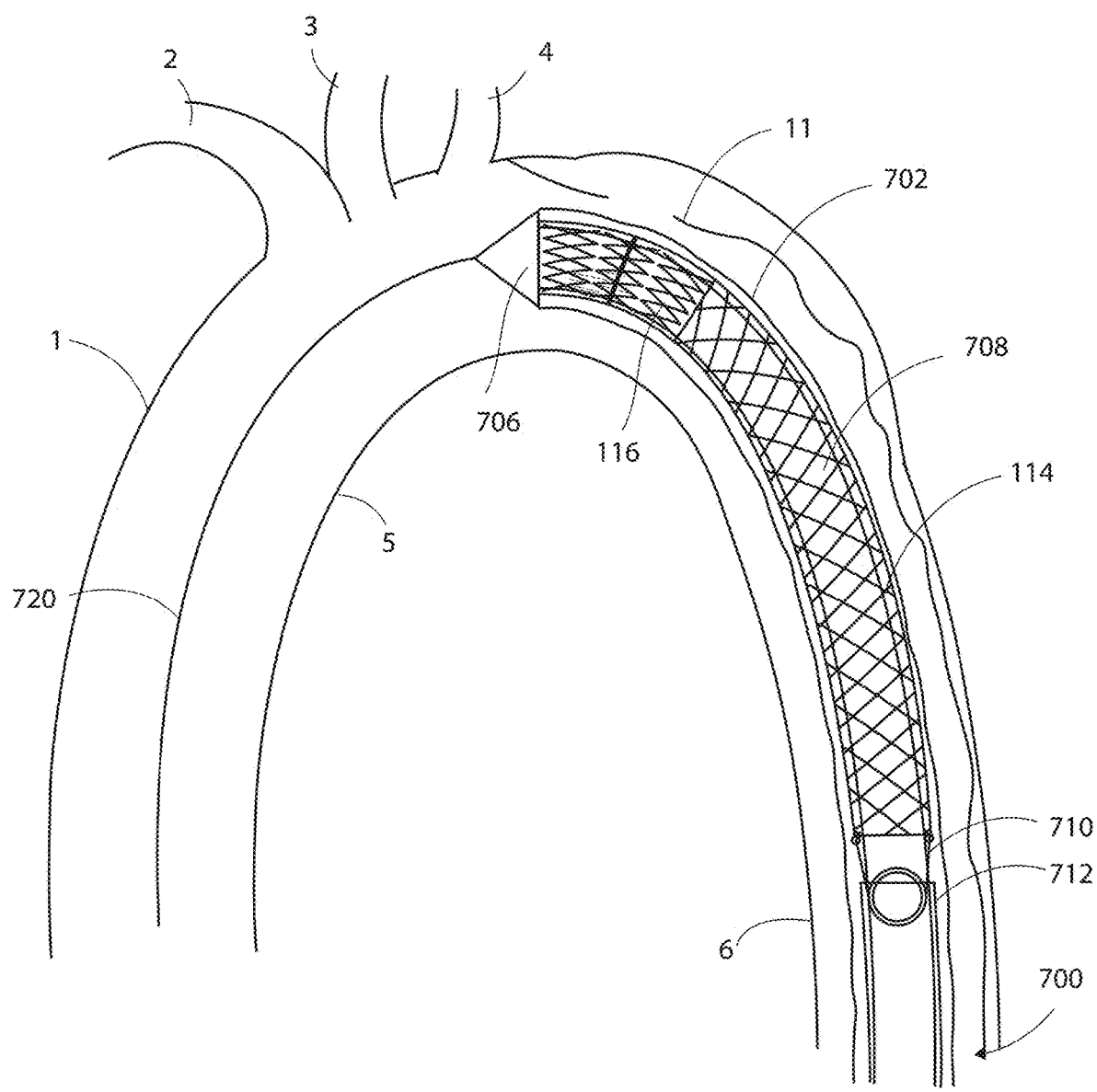
FIG. 12 is a side view of a stent and deployment device being positioned in a thoracic aorta according to one or more embodiments disclosed herein.
Figure 13:
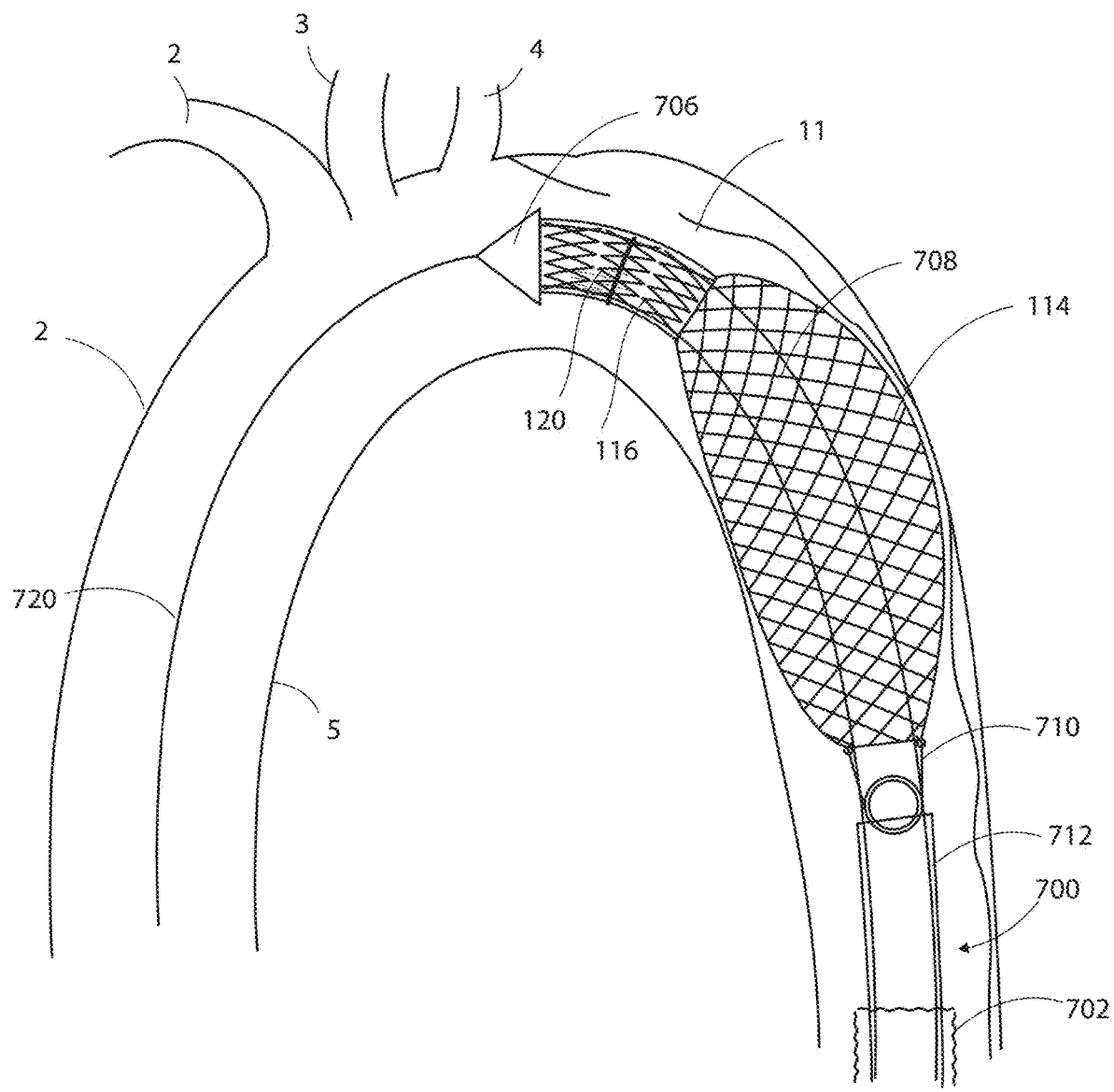
FIG. 13 is a sequential side view where a medial portion of the stent is expanded relative to the stent in FIG. 12 according to one or more embodiments disclosed herein.
Figure 14:
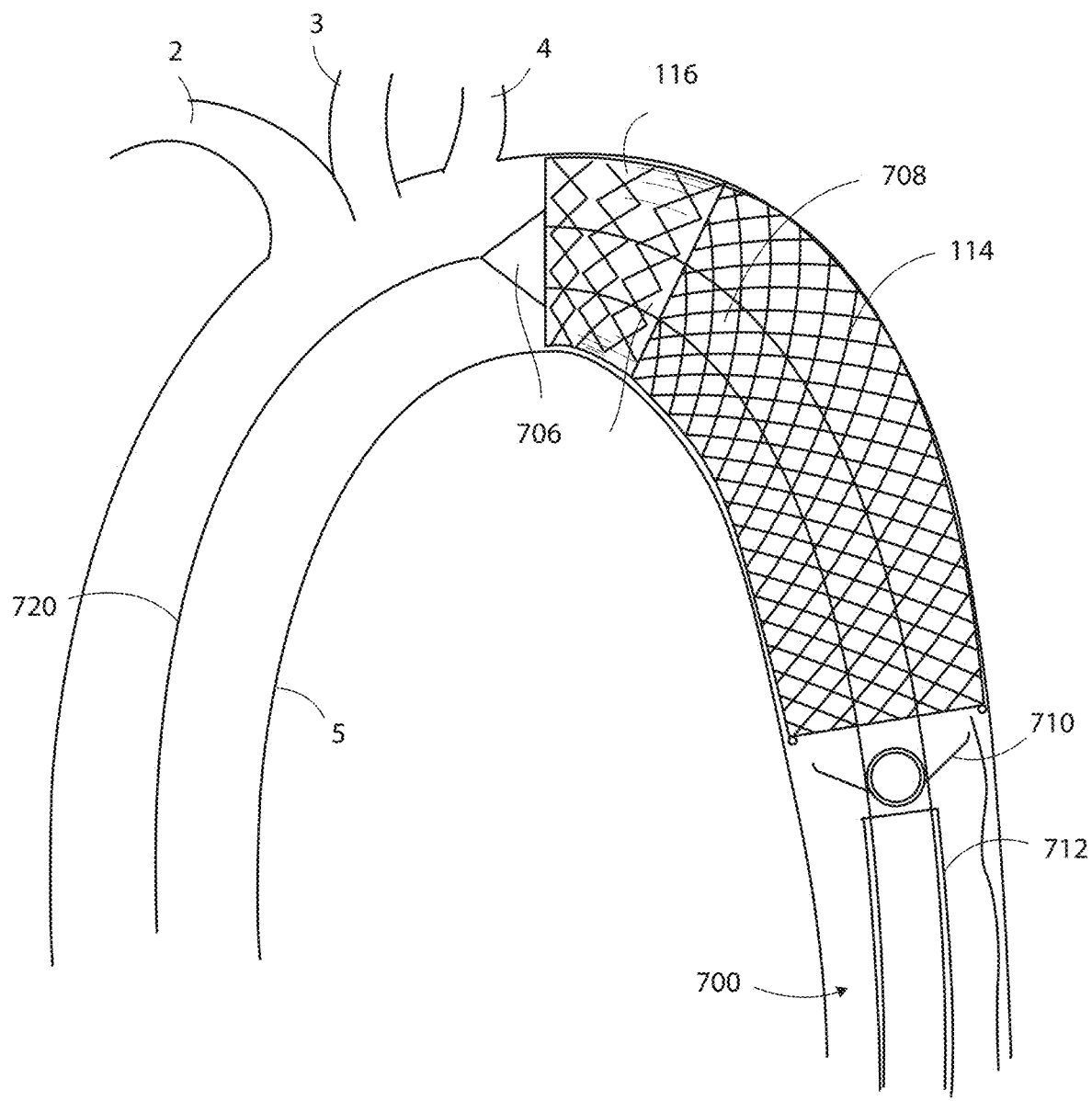
FIG. 14 is a sequential side view where the stent is fully expanded in the aorta according to one or more embodiments disclosed herein.
Figure 15:
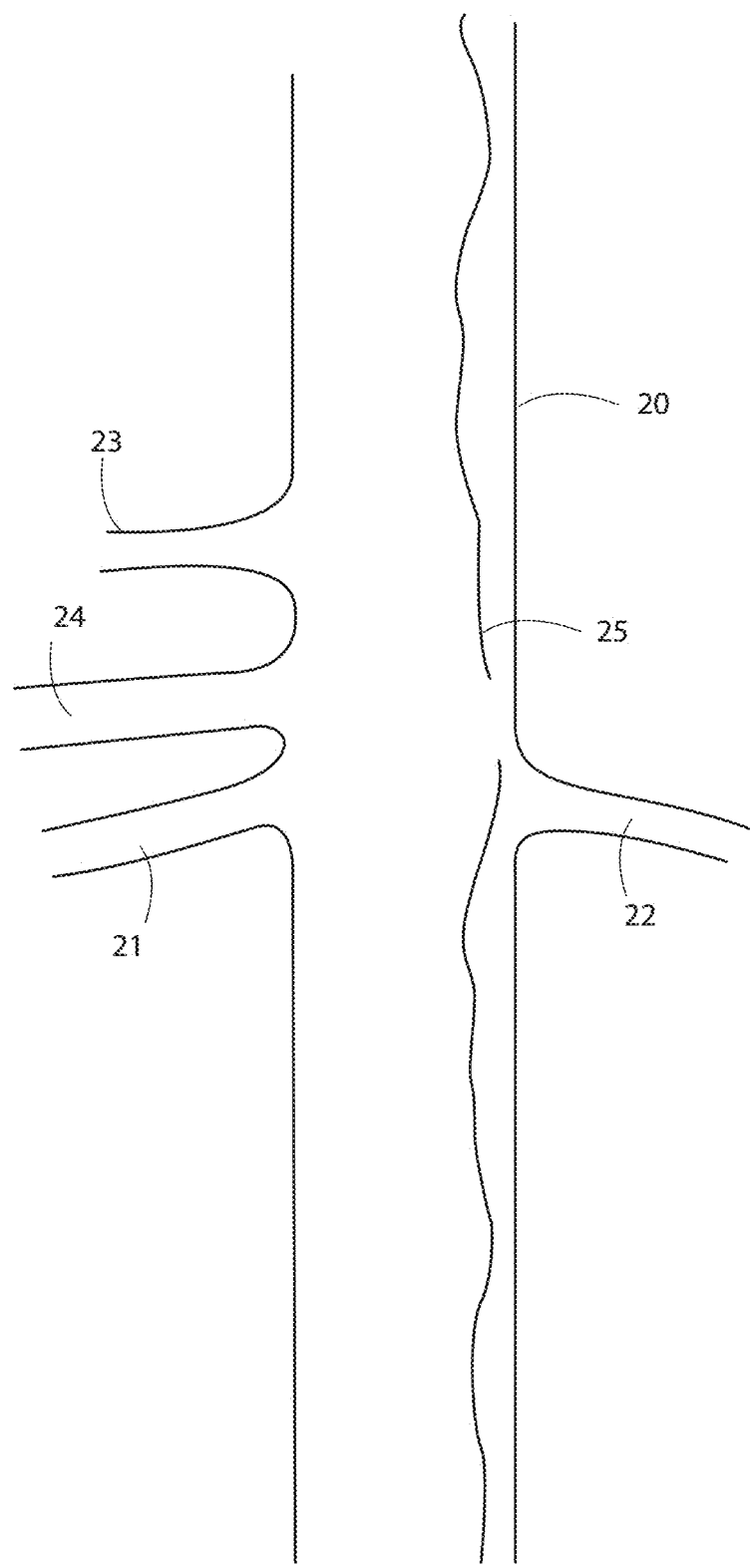
FIG. 15 is a view of an abdominal aorta according to one or more embodiments disclosed herein.
Figure 16:
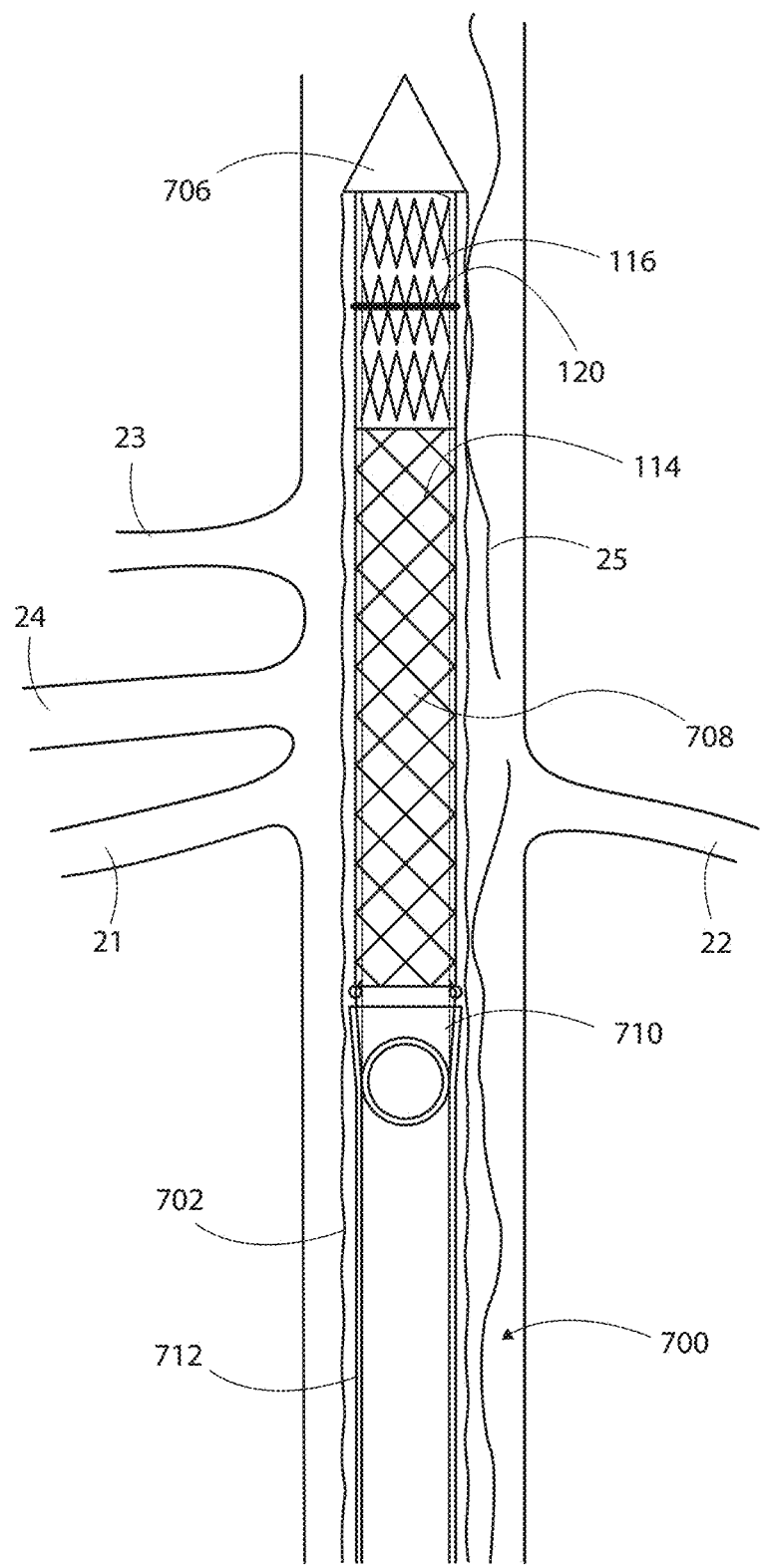
FIG. 16 is a side view of the stent and deployment device positioned in the abdominal aorta according to one or more embodiments disclosed herein.
Figure 17:
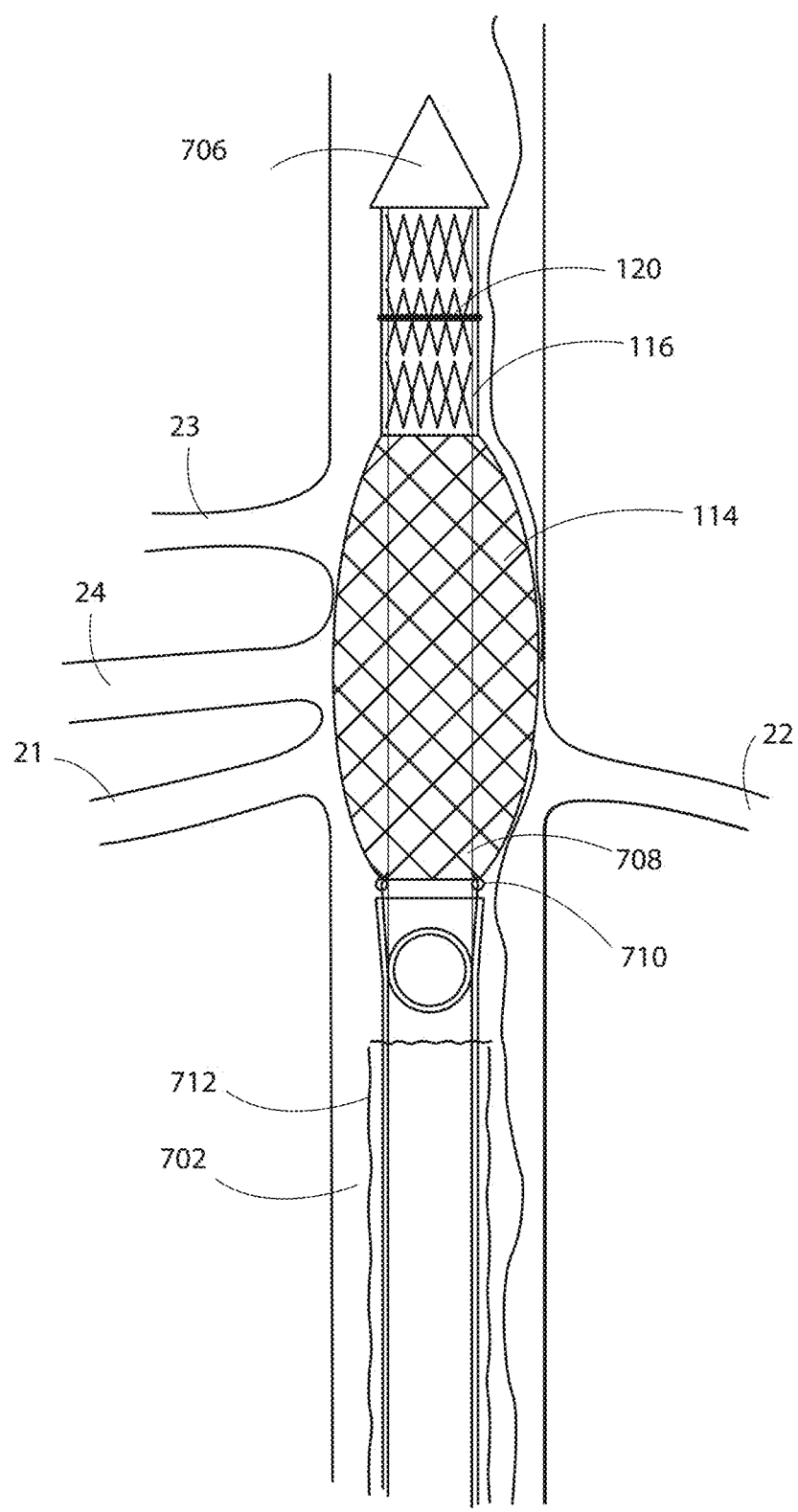
FIG. 17 is a sequential side view of the stent and deployment device where a medial portion of the stent has been expanded relative to the stent in FIG. 16 according to one or more embodiments disclosed herein.
Figure 18:
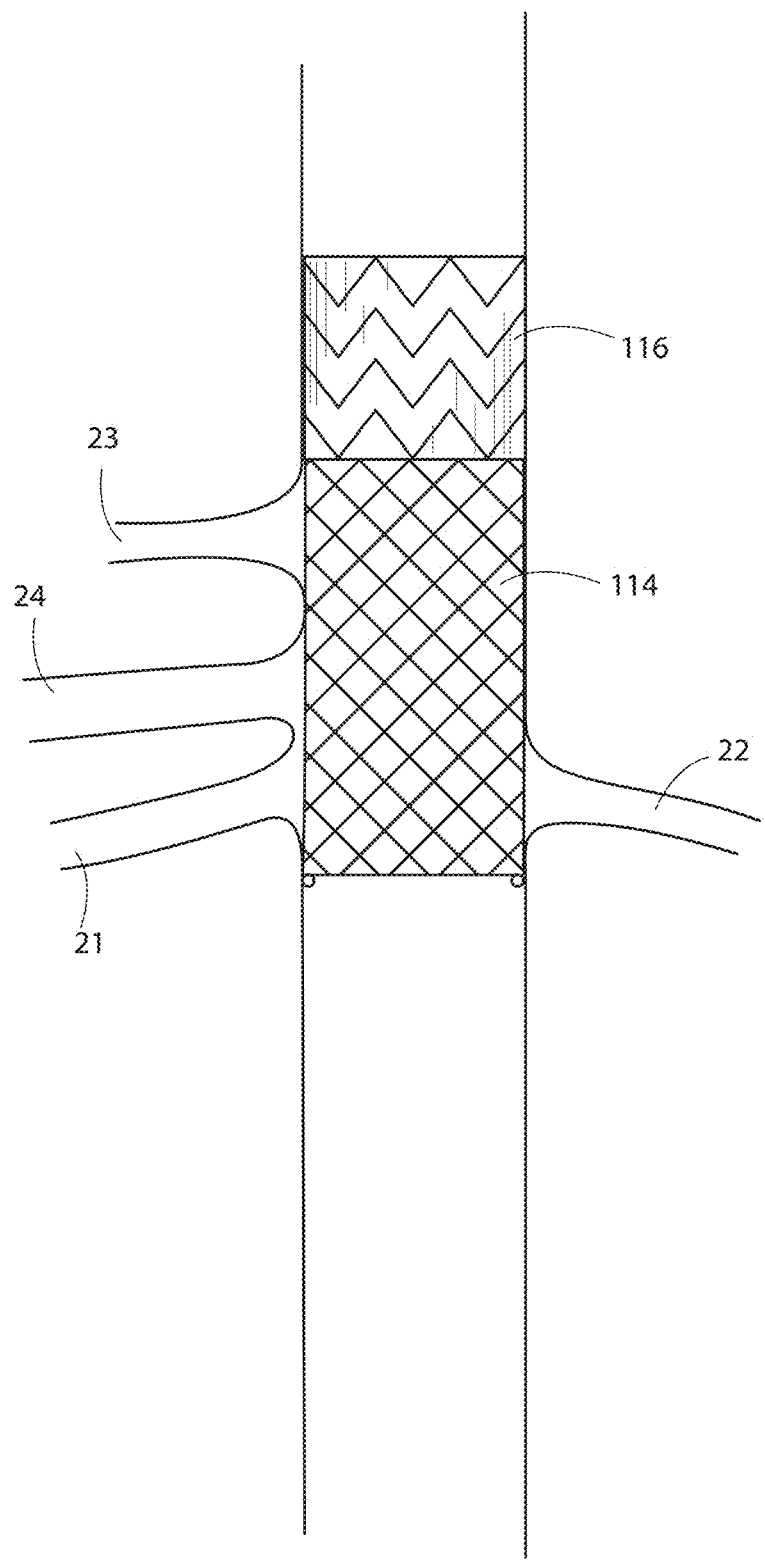
FIG. 18 is a side view of the stent fully expanded within the abdominal aorta according to one or more embodiments disclosed herein.

FIGS. 12 and 13 show the repair of a type B dissection 11 with the proximal covered endograft 116 compressing and closing the proximal tear 11, with the braided stent segment having an adjustable diameter to be able to tack the flap of the dissection back to the aortic wall. Deployment of this device is similar to that which is shown with respect to FIGS. 6 through 11, with the main difference being that the portion 116 is positioned downstream of the left subclavian 4 upon deployment. Similarly to that shown in FIGS. 6 through 11, stent portion 114 is first expanded, and then portion 116 is lastly expanded until finally deployed like shown in FIG. 14. This will tack the intimal flap back to the aortic wall and promote healing of the flap. The remainder of the graft is now deployed.

The device 100 is delivered using the femoral or iliac arteries as access. A wire is passed up into the aorta. Angiogram and intravascular ultrasound (IVUS) is used to identify the tear and the origin of the dissection. The device is passed up to the desired location and deployed.

Deployment of the kit 10 in the abdominal aorta is illustrated in FIGS. 15 through 18. The abdominal aorta 20 includes renal arteries 21 and 22, the celiac trunk 23, and the superior mesenteric artery 24. A dissection 25 is illustrated involving the abdominal aorta and the orifices of the visceral branches. The device 110 is deployed by translating upwardly with the deployment apparatus 700. In this embodiment, each end 112 and 116 of the stent device 110 includes a covering, however, the distal end of the device may be void of any covering. Portion 112 is positioned proximal in the dissection 25. Portion 112 may be positioned further downward of the dissection 25 in anticipation of shortening of the stent device 110, or the operator may push and pull on the deployment device 700 to position the portion 112 proximal the dissection 25 and create the desired expansion of the stent device 110 to fully engage the aorta 20. Deployment is accomplished sequentially in FIGS. 16 through 18 in a manner similar to that described with the ascending aorta or thoracic aorta.

Figure 19:
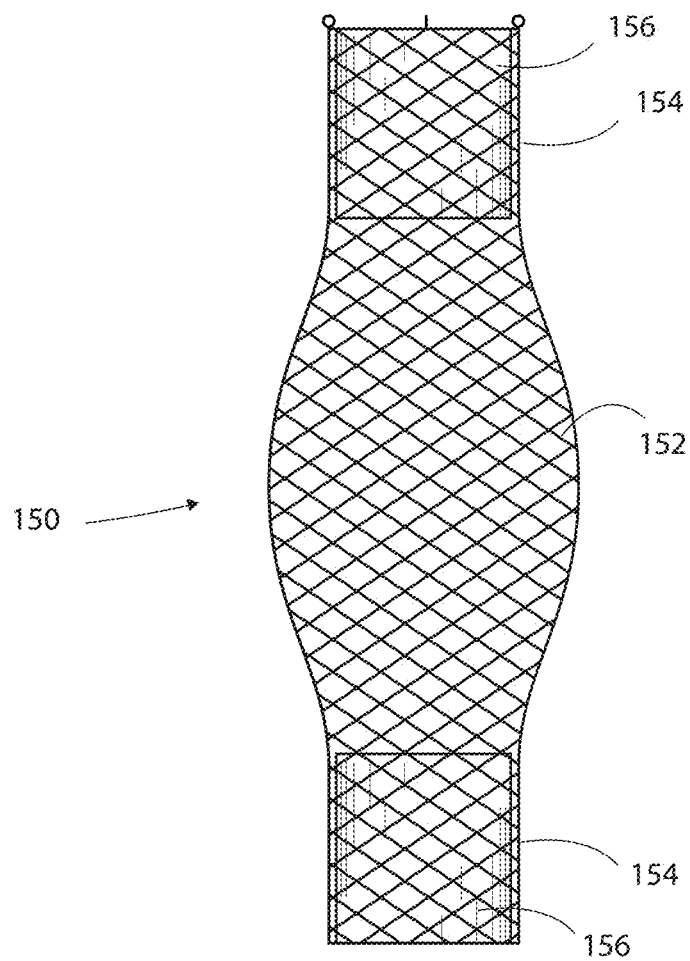
FIGS. 19 through 22 are various illustrations of alternate embodiments of a stent device for use with the deployment apparatuses and methods disclosed herein.
Figure 20:
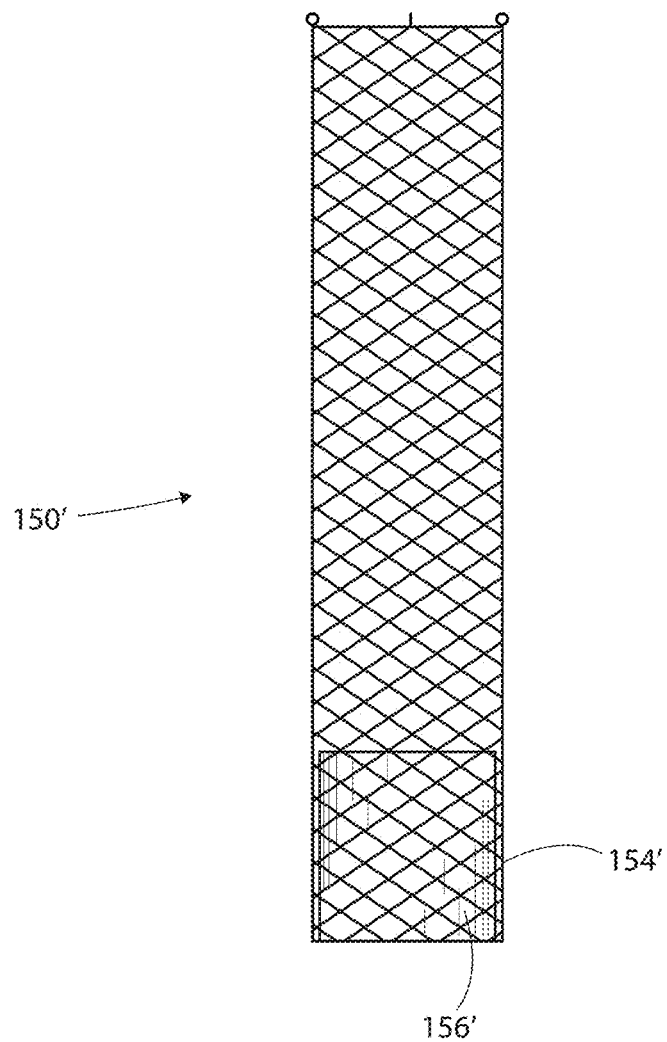

FIG. 19 illustrates a stent device 150 according to an alternate embodiment disclosed herein. The stent device 150 may be deployed with the deployment apparatus and as described with other embodiments disclosed herein. The stent device 150 includes a medial portion 152 and end portions 154. An impermeable prosthesis 156 may be provided on the inside or outside of end portion 154. The impermeable prosthesis 156 may only be provided on one end of end portions 154 in appropriate embodiments such that the other end remains uncovered as illustrated with the stent device 150' shown in FIG. 20, where end portion 154' includes impermeable prosthesis 156, but the other (in this instance, adjacent to the eyelet ends) remains uncovered.

Figure 21:
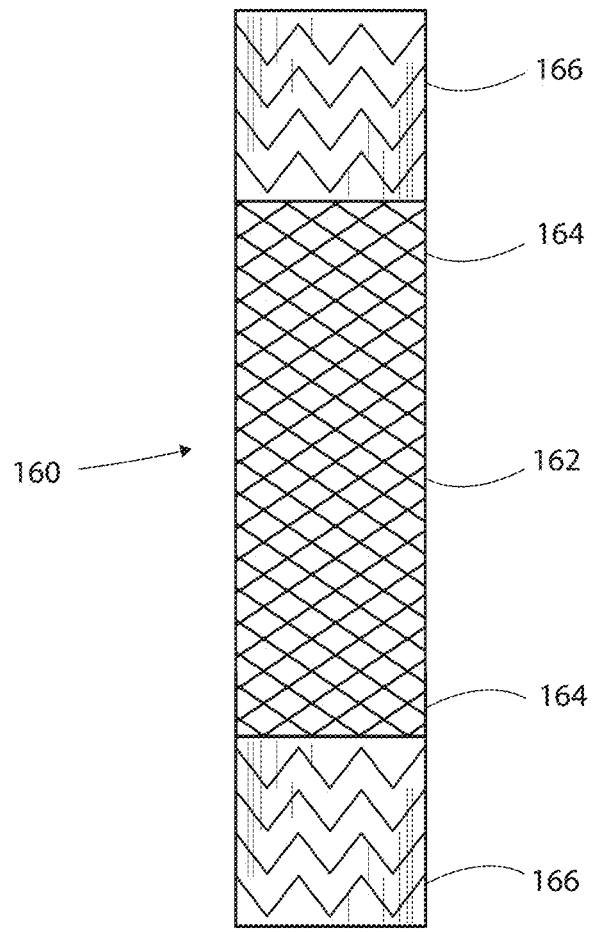
Figure 22:
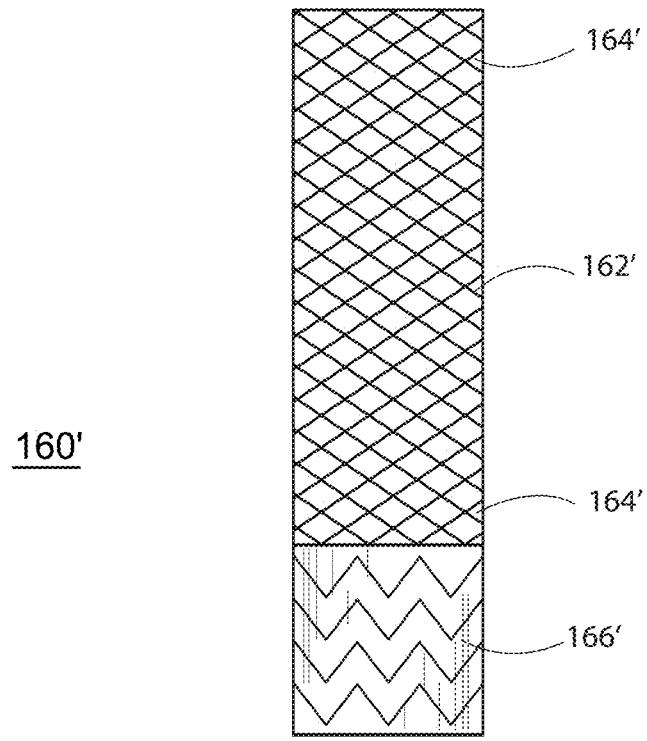

FIG. 21 illustrates a stent device 160 according to an alternate embodiment disclosed herein. The stent device 160 may be deployed with the deployment apparatus and as described with other embodiments disclosed herein. The stent device 160 includes a medial portion 162 and end portions 164. An impermeable prosthesis 166 may be provided in engagement with end portions 164 and may be reinforced with z-stents, oval stents, circular stents, m-shaped stents, and the like. An impermeable prosthesis 166' may only be provided on one end of end portions 164' in appropriate embodiments such that the other end remains uncovered as illustrated with the stent device 160' shown in FIG. 22, where end portion 164' is engaged with impermeable prosthesis 166'.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the disclosure and that the method and apparatus within the scope of these claims and their equivalents be covered thereby. In sum, it should be understood that the disclosure is capable of modification and variation and is limited only by the following claims.

The invention claimed is:

1. A kit comprising:
a stent device for placement in the aorta arch of a patient, wherein a diameter of the stent device may be modified by translation of an end of the stent device to thereby alter a length thereof causing modification of the diameter of the stent device,
wherein the stent device comprises:
a distal stent portion that is permeable,
wherein the distal stent portion is a wireframe assembly that defines a circumferential periphery that spans but does not extend into the brachiocephalic artery, left common carotid artery, and left subclavian artery when placed within the aortic arch of a patient; and
a proximal portion that is impermeable and having a constraining member for constraining a diameter thereof,
wherein the proximal portion engages the distal stent portion at respective ends thereof such that the proximal portion is spaced-apart from the distant stent portion; and
a deployment apparatus comprising a sheath for housing the stent device and having a guide rod passing through a center therethrough for deploying the stent device at an operational site,
wherein the sheath constrains the distal portion of the stent device in a compressed state,
wherein the constraining member constrains the proximal portion of the stent device in a compressed state after removal of the sheath until release of the constraining member, and
wherein the guide rod carries the stent device and is removable through a center of the stent device when the stent device is in an expanded state and positioned within the aortic arch of the patient upon removal of the sheath.

2. The kit of claim 1, wherein the stent device includes at least one eyelet on a first end facing an operator, and the deployment apparatus further includes a pawl that is configured to engage the eyelet to expand and contract the end of the stent device to thereby shorten and elongate the stent device.

3. The kit of claim 2, wherein the pawl is initially retracted to contract the end of the stent device.

4. The kit of claim 3, wherein the pawl is initially retracted by a sleeve extending thereabout and the sleeve is translatable away from the pawl to thereby expand the pawl.

5. The kit of claim 3, wherein the pawl and the sleeve are translatable relative to the guide rod to alter one or more dimensions of the stent device.

6. The kit of claim 1, further including a guide wire extending through the guide rod and through a bumper on a second end opposed to the operator.

7. The kit of claim 6, wherein the proximal portion is covered with graft material.

8. The kit of claim 7, wherein the proximal portion covered with graft material includes a supporting wire frame.

9. The kit of claim 6, wherein the second end is telescopically engaged with a prosthetic device engaged in an adjacent anatomical organ.

10. The kit of claim 1, wherein the guide rod has a major external diameter that is about equal to an interior diameter of the stent device in the compressed state.

11. The kit of claim 10, wherein the prosthetic device is a transcatheter stent valve.

\* \* \* \* \*